United States Patent [19]
Weichert et al.

[11] Patent Number: 6,075,054
[45] Date of Patent: Jun. 13, 2000

[54] ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

[75] Inventors: Andreas Weichert, Egelsbach; Joachim Brendel, Bad Vilbel; Heinz-Werner Kleemann, Bischofsheim; Hans Jochen Lang, Hofheim; Jan-Robert Schwark, Frankfurt; Udo Albus, Florstadt; Wolfgang Scholz, Eschborn, all of Germany

[73] Assignee: Hoechst Aktiengesellschaft, Frankfurt am Main, Germany

[21] Appl. No.: 09/028,474

[22] Filed: Feb. 24, 1998

[30] Foreign Application Priority Data

Apr. 1, 1997 [DE] Germany .............. 197 13 427

[51] Int. Cl.$^7$ .................................. A61K 31/165
[52] U.S. Cl. .................. 514/617; 514/622; 514/634; 564/176; 564/237
[58] Field of Search ................. 564/237, 176; 514/617, 622, 634

[56] References Cited

U.S. PATENT DOCUMENTS 5,747,539  5/1998  Dorsch et al. ................ 514/618
5,856,574  1/1999  Weichert et al. ............... 564/183

FOREIGN PATENT DOCUMENTS 0 640 588 A1  8/1994  European Pat. Off. .
0 704 431 A2  4/1996  European Pat. Off. .
0 814 077 A1  12/1997  European Pat. Off. .

OTHER PUBLICATIONS

English Language Abstract of EP 0 640 588 A1 (Derwent Abstract No. 95–092257).
English Language Abstract of EP 0 704 431 A2 (Derwent Abstract No. 96–130135).
English Language Abstract of EP 0 814 077 A1 (Derwent Abstract No. 98–044281).

*Primary Examiner*—Samuel Barts
*Attorney, Agent, or Firm*—Finnegan, Henderson, Farabow, Garrett & Dunner, L.L.P.

[57] ABSTRACT

Benzoylguanidines of formula I

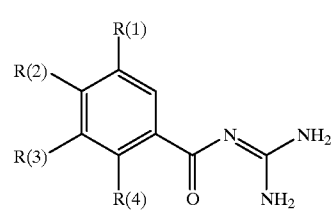

with R(1) to R(4) as defined in the specification, are suitable as antiarrhythmic pharmaceuticals having a cardioprotective component for infarct prophylaxis and infarct treatment as well as for the treatment of angina pectoris.

They inhibit, in a preventive manner, the pathophysiological processes in the formation of ischemically induced damage, in particular in the elicitation of ischemically induced cardiac arrhythmias.

9 Claims, No Drawings

ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

FIELD OF THE INVENTION

The invention relates to benzoylguanidines of formula I

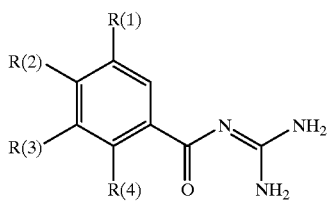

in which:

R(1) is $CF_3$;

one of the substituents R(2) and R(3) is hydrogen;

and the other substituent R(2) or R(3) in each case is —C(OH)($CH_3$)—$CH_2$OH, —CH($CH_3$)—$CH_2$OH or —C(OH)($CH_3$)$_2$;

R(4) is methyl, methoxy, Cl or $CF_3$;

or pharmaceutically tolerable salts thereof.

Preferred compounds of formula I are those in which

R(1) is $CF_3$;

one of the substituents R(2) and R(3) is hydrogen;

and the other substituent R(2) or R(3) in each case is —C(OH)($CH_3$)—$CH_2$OH, —CH($CH_3$)—$CH_2$OH or —C(OH)($CH_3$)$_2$;

R(4) is methyl;

or pharmaceutically tolerable salts thereof.

Particularly preferred compounds of formula I are those in which:

R(l) is $CF_3$;

one of the substituents R(2) and R(3) is hydrogen;

and the other substituent R(2) or R(3) in each case is —CH($CH_3$)—$CH_2$OH;

R(4) is methyl;

or pharmaceutically tolerable salts thereof.

A very particularly preferred compound of formula I is that in which:

R(1) is $CF_3$;

R(2) is —CH($CH_3$)—$CH_2$OH;

R(3) is hydrogen;

R(4) is methyl;

or pharmaceutically tolerable salts thereof.

If one of the substituents R(2) or R(3) contains a center of asymmetry, it can have either S or R configuration. The compounds can be present as optical isomers, as diastereomers, as racemates, or as mixtures thereof.

The invention additionally relates to a process for the preparation of a compound of formula I, which comprises reacting a compound of formula II

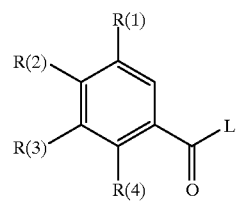

in which R(1) to R(4) have the meaning indicated above and L is an easily nucleophilically substitutable leaving group, with guanidine.

The activated acid derivatives of formula II, in which L is an alkoxy group, preferably a methoxy group, a phenoxy group, phenylthio group, methylthio group or 2-pyridylthio group, a nitrogen heterocycle, preferably 1-imidazolyl, are advantageously obtained in a manner known per se from the carboxylic acid chlorides on which they are based (formula II, L=Cl), which for their part can in turn be prepared in a manner known per se from the carboxylic acids on which they are based (formula II, L=OH), for example, using thionyl chloride.

Beside the carboxylic acid chlorides of formula II (L=Cl), other activated acid derivatives of formula II can also be prepared from the benzoic acid derivatives on which they are based (formula II, L=OH) in a manner known per se, such as the methyl esters of formula II with L=$OCH_3$ by treating with gaseous HCl in methanol, the imidazolides of formula II by treating with carbonyldiimidazole (L=1-imidazolyl, Staab, *Angew. Chem. Int. Ed. Engl.* 1, 351–367 (1962) incorporated by reference herein), the mixed anhydrides II with Cl—$COOC_2H_5$ or tosyl chloride in the presence of triethylamine in an inert solvent, and the activation of benzoic acids with dicyclohexylcarbo-diimide (DCC) or with O-{(cyano(ethoxycarbonyl)methylene)amino}-1,1,3, 3-tetramethyluronium-tetrafluoroborate ("TOTU") (*Proceedings of the 21st European Peptide Symposium, Peptides* 1990 Eds. E. Giralt and D. Andreu, Escom, Leiden, 1991, incorporated herein by reference). A number of suitable methods for the preparation of activated carboxylic acid derivatives of formula II are given with details of the source literature in J. March, *Advanced Organic Chemistry*, Third Edition (John Wiley & Sons, 1985), p. 350, which is herein incorporated by reference.

The reaction of an activated carboxylic acid derivative of formula II with guanidine is carried out in a manner known per se in a protic or aprotic polar but inert organic solvent. In the reaction of the methyl benzoates (formula II, L=OMe) with guanidine, methanol, isopropanol or THF from 20° C. up to the boiling temperature of these solvents has proven suitable. Most reactions of compounds of formula II with salt-free guanidine were advantageously carried out in aprotic inert solvents such as THF, dimethoxyethane or dioxane. However, when using a base such as, for example, NaOH, water can be used as solvent in the reaction of formula II with guanidine.

When L=Cl, the reaction is advantageously carried out with addition of an acid scavenger, e.g. in the form of excess guanidine, for the binding of the hydrohalic acid.

Some of the underlying benzoic acid derivatives of formula II are known and described in the literature. The unknown compounds of formula II can be prepared by methods known from the literature. The benzoic acids obtained are reacted by one of the process variants described above to give compounds of formula I according to the invention.

The introduction of the substituents in the 2-, 3-, 4- and 5-positions is carried out by methods known from the literature of palladium-mediated cross-coupling of aryl halides or aryl triflates with, for example, organostannanes, organoboronic acids or organoboranes or organocopper or -zinc compounds.

In general, benzoylguanidines of formula I are weak bases and can bind acid with formation of salts. Possible acid addition salts are salts of all pharmacologically tolerable acids, for example halides, in particular hydrochlorides, lactates, sulfates, citrates, tartrates, acetates, phosphates, methylsulfonates and p-toluenesulfonates.

The compounds of formula I are substituted acylguanidines.

Compounds similar to the compounds of formula I according to the invention are disclosed in European Offenlegungsschrift 640 588 (HOE 93/F 254), under whose formula come the compounds according to the invention. The compounds of formula I are distinguished, however, compared with the known compounds by an unusually and surprisingly much higher activity in the inhibition of $Na^+/H^+$ exchange, associated with an excellent water solubility.

Like the known compounds, they have no undesired and disadvantageous salidiuretic properties, but very good antiarrhythmic properties, such as are important, for example, for the treatment of illnesses which occur in the case of oxygen deficiency symptoms.

On account of their pharmacological properties, the compounds are outstandingly suitable as antiarrhythmic pharmaceuticals having a cardioprotective component for infarct prophylaxis and infarct treatment and also for the treatment of angina pectoris, where they also inhibit or greatly decrease, in a preventive manner, the pathophysiological processes in the formation of ischemically induced damage, in particular in the elication of ischemically induced cardiac arrhythmias. Because of their protective actions against pathological hypoxic and ischemic situations, the compounds of formula I according to the invention can be used on account of inhibition of the cellular $Na^+/H^+$ exchange mechanism as pharmaceuticals for the treatment of all acute or chronic damage caused by ischemia or illnesses induced primarily or secondarily thereby. This relates to their use as pharmaceuticals for surgical interventions, e.g. in organ transplantation, where the compounds can be used both for the protection of the organs in the donor before and during removal, for the protection of removed organs, for example during treatment with or storage thereof in physiological bath fluids, and during transfer to the recipient's body.

The compounds are likewise valuable, protective pharmaceuticals when carrying out angioplastic surgical interventions, for example on the heart, and on peripheral vessels. Corresponding to their protective action against ischemically induced damage, the compounds are also suitable as pharmaceuticals for the treatment of ischemias of the nervous system, in particular of the central nervous system, where they are suitable, for example, for the treatment of stroke or of cerebral edema. Moreover, the compounds of formula I according to the invention are likewise suitable for the treatment of forms of shock, such as, for example, of allergic, cardiogenic, hypovolemic and bacterial shock.

Moreover, the compounds of formula I according to the invention are distinguished by strong inhibitory action on the proliferation of cells, for example of fibroblast cell proliferation and the proliferation of vascular smooth muscle cells. The compounds of formula I are therefore suitable as valuable therapeutics for illnesses in which cell proliferation is a primary or secondary cause, and can therefore be used as anti-atherosclerotics, agents against diabetic late complications, carcinomatous disorders, fibrotic disorders such as pulmonary fibrosis, hepatic fibrosis or renal fibrosis, organ hypertrophy and hyperplasia, in particular in prostate hyperplasia or prostate hypertrophy.

The compounds according to the invention are valuable inhibitors of the cellular sodium-proton antiporter ($Na^+/H^+$ exchanger), which is raised in numerous disorders (essential hypertension, atherosclerosis, diabetes etc.), even in those cells which are easily accessible to measurement, such as, for example, in erythrocytes, platelets or leucocytes. The compounds according to the invention are therefore suitable as excellent and simple scientific tools, for example in their use as diagnostics for the determination and differentiation of certain forms of hypertension, but also of atherosclerosis, of diabetes, proliferative disorders etc. Moreover, the compounds of formula I are suitable for preventive therapy for the prevention of the genesis of high blood pressure, for example of essential hypertension.

Additionally, the compounds of formula I have a favorable effect on serum lipoproteins. It is generally recognized that for the formation of arteriosclerotic vascular changes, in particular of coronary heart disease, excessively high blood lipid values, so-called hypolipoproteinemias, are a significant risk factor. The lowering of raised serum lipoproteins is therefore of extreme importance for the prophylaxis and the regression of atherosclerotic changes. Beside the reduction of the serum total cholesterol, the lowering of the proportion of specific atherogenic lipid fractions of this total cholesterol, in particular of the low density lipoproteins (LDL) and of the very low density lipoproteins (VLDL) is of particular importance, since these lipid fractions are an atherogenic risk factor. On the other hand, the high density lipoproteins are ascribed a protective function against coronary heart disease. Accordingly, hypolipidemics should be able to lower not only the total cholesterol, but in particular the VLDL and LDL serum cholesterol fractions. The compounds of formula I have valuable therapeutically utilizable properties with respect to the influencing of the serum lipid levels. Thus, they significantly reduce the raised serum concentration of LDL and VLDL, such as are to be observed, for example, due to increased dietetic intake of a cholesterol- and lipid-rich diet or in the case of pathological metabolic changes, for example genetically related hypolipidemias. They can therefore be used for the prophylaxis and for the regression of atherosclerotic changes by switching off a causal risk factor. These include not only the primary hypolipidemias, but also certain secondary hypolipidemias, such as occur, for example, in diabetes. Moreover, the compounds of formula I result in a distinct reduction of the infarcts induced by metabolic anomalies and in particular to a significant decrease in the induced infarct size and its degree of severity. Furthermore, compounds of formula I result in effective protection against endothelial damage induced by metabolic anomalies. With this protection of the vessels against the endothelial dysfunction syndrome, compounds of formula I are valuable pharmaceuticals for the prevention and for the treatment of coronary vasospasms, of atherogenesis and of atherosclerosis, left-ventricular hypertrophy and of dilated cardiomyopathy, and of thrombotic disorders.

The compounds mentioned are therefore used advantageously for the production of a medicament for the treatment of hypercholesterolemia; for the production of a medicament for the prevention of atherogenesis; for the production of a medicament for the prevention and treatment of atherosclerosis, for the production of a medicament for the prevention and treatment of illnesses which are caused by raised cholesterol levels, for the production of a medicament for the prevention and treatment of illnesses which are caused by endothelial dysfunction, for the production of a medicament for the prevention and treatment or atherosclerosis-induced hypertension, for the production of a medicament for the prevention and treatment of atherosclerosis-induced thromboses, for the production of a medicament for the prevention and treatment of hypercholesterolemia- and endothelial dysfunction-induced ischemic damage and postischemic reperfusion damage, for the production of a medicament for the prevention and treatment of hypercholesterolemia- and endothelial dysfunction-induced cardiac hypertrophy and cardiomyopathy, for the production of a medicament for the prevention and treatment of hypercholesterolemia- and endothelial dysfunction-induced coronary vasospasms and myocardial infarcts, for the production of a medicament for the treatment of the conditions mentioned in combinations with hypotensive substances, preferably with angiotensin-converting enzyme (ACE) inhibitors and angiotensin receptor antagonists, a combination of an NHE inhibitor of formula I with a blood lipid level-lowering active compound, preferably with an HMG-CoA reductase inhibitor (e.g. lovastatin or pravastatin), where the latter produces a hypolipidemic action and thereby increases the hypolipidemic properties of the NHE inhibitor of formula I, proving to be a favorable combination with increased action and decreased use of active compound.

The administration of sodium-proton exchange inhibitors of formula I is claimed as novel pharmaceuticals for lowering raised blood lipid levels, as well as the combination of sodium-proton exchange inhibitors with hypotensive and/or hypolipidemic pharmaceuticals.

Pharmaceuticals that contain a compound of formula I can be administered orally, parenterally, intravenously, rectally or by inhalation, the preferred administration being dependent on the particular form of the disorder. The compounds of formula I can be used on their own or together with pharmaceutical auxiliaries, namely both in veterinary and in human medicine.

The person skilled in the art is familiar on the basis of his expert knowledge with the auxiliaries that are suitable for the desired pharmaceutical formulation. Besides solvents, gel-forming agents, suppository bases, tablet auxiliaries and other active compound carriers, it is possible to use, for example, antioxidants, dispersants, emulsifiers, antifoams, flavor corrigents, preservatives, solubilizers or colorants.

For a form for oral administration, the active compounds are mixed with the additives suitable therefor, such as excipients, stabilizers or inert diluents and are brought by the customary methods into the suitable administration forms, such as tablets, coated tablets, hard capsules, aqueous, alcoholic or oily solutions. Inert carriers which can be used, are, for example, gum arabic, magnesium, magnesium carbonate, potassium phosphate, lactose, glucose or starch, in particular maize starch. Preparation can be carried out both as dry and as moist granules. Suitable oily excipients or solvents are, for example, vegetable or animal oils, such as sunflower oil or cod liver oil.

For subcutaneous or intravenous administration, the active compounds, if desired with the substances customary therefore such as solubilizers, emulsifiers or other auxiliaries, are brought into solution, suspension or emulsion. Possible solvents are, for example: water, physiological saline solution or alcohols, e.g. ethanol, propanol, glycerol, and in addition also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of a reactive compound of formula I in a pharmaceutically acceptable solvent, such as, in particular, ethanol or water, or a mixture of such solvents.

If required, the formulation can also contain other pharmaceutical auxiliaries such as surfactants, emulsifiers and stabilizers, as well as a propellant. Such a preparation contains the active compound customarily in a concentration from approximately 0.1 to 10% by weight, in particular from approximately 0.3 to 3% by weight.

The dose of the active compound of formula I to be administered and the frequency of administration depend on the potency and duration of action of the compounds used; additionally also on the nature and severity of the illness to be treated and on the sex, age, weight and individual responsiveness of the mammal to be treated.

On average, the daily dose of a compound of formula I in the case of a patient weighing approximately 75 kg is at least 0.001 mg/kg, preferably 0.01 mg/kg, to at most 10 mg/kg, preferably 1 mg/kg, of body weight. In acute episodes of the illness, for example immediately after suffering a cardiac infarct, even higher and, especially, more frequent doses may also be necessary, e.g. up to 4 individual doses per day. In particular in the case of i.v. administration, for example in the case of an infarct patient in the intensive care unit, up to 200 mg per day may be necessary.

List of abbreviations:
MeOH Methanol
DMF N,N-Dimethylformamide
RT Room temperature
EA Ethyl acetate (EtOAc)
EI Electron impact
ES Electrospray ionization
m.p. Melting point
THF Tetrahydrofuran
eq. Equivalent Experimental Section General procedure for the preparation of benzoylguanidines (I)

Variant A: from benzoic acids (formula II, L=OH)

1.0 eq. of the benzoic acid derivative of formula II is dissolved or suspended in anhydrous THF (5 ml/mmol) and then treated with 1.1 eq. of carbonyldiimidazole. After stirring at RT for 2 hours, 5.0 eq. of guanidine are introduced into the reaction solution. After stirring overnight, the THF is distilled off under reduced pressure (rotary evaporator), the residue is treated with water, the mixture is adjusted to pH 6 to 7 using 2 N HCl and the corresponding benzoylguanidine (formula I) is filtered off. The benzoylguanidines thus obtained can be converted into the corresponding salts by treating with aqueous, methanolic or ethereal hydrochloric acid or other pharmacologically tolerable acids.

General procedure for the preparation of benzoylguanidines (I)

Variant B: from alkyl benzoates (formula II, L=O-alkyl)

1.0 eq. of the alkyl benzoate of formula II and 5.0 eq. of guanidine (free base) are dissolved in isopropanol or suspended in THF and heated to boiling (typical reaction time 2 to 5 h) until conversion is complete (thin-layer chromatography determination). The solvent is distilled off under reduced pressure (rotary evaporator), the residue is taken up in EA and the mixture is washed 3× with NaHCO$_3$ solution.

It is dried over $Na_2SO_4$, the solvent is distilled off in vacuo and the residue is chromatographed on silica gel using a suitable eluent, e.g. EA/MeOH 5:1. (Salt formation compare Variant A)

EXAMPLE 1

4-(1'-Hydroxy-2'-propyl)-2-methyl-5-trifluoroethylbenzoyl-guanidine hydrochloride, colorless crystals, decomposition from 100° C., MS (ES): $M^++H=304$

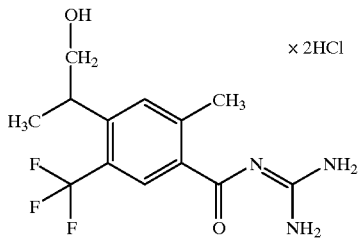

Synthesis route:

a) Methyl 4-hydroxy-2-chloro-5-iodobenzoate from methyl 4-hydroxy-2-chlorobenzoate by Olah iodination with 1 eq. of N-iodosuccinimide in 5 eq. of trifluoromethanesulfonic acid at RT for 24 h, colorless crystals, m.p. 188–89° C., MS (EI): $M^+=312$.

b) Methyl 4-benzyloxy-2-chloro-5-iodobenzoate from 1a) by reaction with 1 eq. of benzyl bromide in the presence of 1.5 eq. of potassium carbonate in absolute DMF at RT. Aqueous work-up followed by recrystallization from i-propanol affords colorless crystals, m.p. 107–08° C., MS(ES): $M^++H=403$.

c) Methyl 4-benzyloxy-2-chloro-5-trifluoromethylbenzoate from 1b) reaction with 1 eq. of potassium trifluoroacetate and 1.1 eq. of copper(I) iodide in DMF under reflux. Column-chromatographic work-up affords colorless solid, m.p. 127–28° C., MS (ES): $M^++H=345$.

d) Methyl 4-benzyloxy-2-methyl-5-trifluoroethylbenzoate from 1c) by cross-coupling with 5 eq. of methylzinc chloride in THF/DMF under reflux in the presence of 0.1 eq. of palladium(II) acetate catalyst, 0.2 eq. of triphenylphosphine and 0.11 eq. of copper(I) iodide, aqueous work-up, extraction with ethyl acetate and subsequent column chromatography on silica gel yields a colorless solid, m.p. 105° C., MS (ES): $M^++H=325$.

e) Methyl 4-hydroxy-2-methyl-5-trifluoromethylbenzoate from 1d) by hydrogenolysis in the presence of palladium/carbon (10%) in methanol at RT. Addition of cyclohexane causes cyrstallization of a colorless solid, m.p. 162–63° C., MS (ES): $M^+H=235$.

f) Methyl 4-trifluoromethanesulfonyloxy-2-methyl-5-trifluoromethylbenzoate from 1e) by reaction with 1.1 eq. of trifluoromethanesulfonic anhydride in the presence of 1.1 eq. of triethylamine in absolute methylene chloride at 0° C. Column chromatography affords an amorphous solid.

g) Methyl 4-isopropenyl-2-methyl-5-trifluoromethylbenzoate from 1f) by cross-coupling with 5 equivalents of isopropenylzinc chloride in THF/DMF under reflux in the presence of 0.1 eq. of palladium(II) acetate catalyst, 0.2 eq. of triphenylphosphine and 0.11 eq. of copper(I) iodide, aqueous work-up, extraction with ethyl acetate and subsequent column chromatography on silica gel yields a colorless oil, MS (ES): $M^++H=259$.

h) Methyl 4-(1'-hydroxy-2'-propyl)-2-methyl-5-trifluoromethylbenzoate from 1g) by hydroboration with 1.05 eq. of borane/tetrahydrofuran complex and subsequent oxidative reaction procedure (alkaline hydrogen peroxide). After aqueous work-up and column-chromatographic purification, a colorless oil is obtained, MS (ES): $M^++H=277$.

i) 4-(1'-Hydroxy-2'-propyl)-2-methyl-5-trifluoromethylbenzoylguanidine hydrochloride from 1h) according to the general procedure, variant B.

Pharmacological data:

Inhibition of the $Na^+/H^+$ exchanger of rabbit erythrocytes White New Zealand rabbits (Ivanovas) received a standard diet with 2% cholesterol for six weeks in order to activate the $Na^+/H^+$ exchange and thus to be able to determine the $Na^+$-influx into the erythrocytes via $Na^+/H^+$ exchange by flame photometry. The blood was taken from the auricular arteries and rendered incoagulable by 25 IU of potassium-heparin. A part of each sample was used for the duplicate determination of the hematocrits by centrifugation. Aliquots of 100 µl in each case were used for the measurement of the $Na^+$ starting content of the erythrocytes.

In order to determine the amiloride-sensitive sodium influx, 100 µl of each blood sample were incubated in 5 ml in each case of a hyperosmolar salt-sucrose medium (mmol/l: 140 NaCl, 3 KCl, 150 sucrose, 0.1 ouabain, 20 tris-hydroxymethylaminomethane) at pH 7.4 and 37° C. The erythrocytes were then washed three times with ice-cold $MgCl_2$-ouabain solution (mmol/l: 112 $MgCl_2$, 0.1 ouabain) and hemolyzed in 2.0 ml of distilled water. The intracellular sodium content was determined by flame photometry.

The $Na^+$ net influx was calculated from the difference between sodium starting values and the sodium content of the erythrocytes after incubation. The amiloride-inhibitable sodium influx followed from the difference in the sodium content of the erythrocytes after incubation with and without amiloride $3 \times 10^{-4}$ mol/l. The procedure was also the same in the case of the compounds according to the invention.

Results

Inhibition of the $Na^+/H^+$ exchanger:

Example $IC_{50}$(mol/l)
1 $0.0012 \times 10^{-6}$

What is claimed is:

1. A benzoylguanidine of formula I

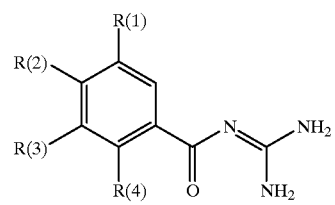

or a pharmaceutically tolerable salt therof, wherein:
R(1) is $CF_3$;
one of the substituents R(2) and R(3) is hydrogen;
and the other substituent, R(2) or R(3), is —C(OH)($CH_3$)—$CH_2$OH, —CH($CH_3$)—$CH_2$OH or —C(OH)($CH_3$)$_2$;
R(4) is methyl, methoxy, Cl or $CF_3$.

2. A compound according to claim 1, wherein R(4) is methyl.

3. A compound according to claim 1, wherein one of the substituents R(2) and R(3) is hydrogen and the other substituent, R(2) or R(3), is —CH($CH_3$)—$CH_2$OH, and wherein R(4) is methyl.

4. A compound according to claim 1, wherein R(2) is —CH($CH_3$)—$CH_2$OH, R(3) is hydrogen, and R(4) is methyl.

5. A process for preparing a compound according to claim 1, comprising reacting a compound of formula II

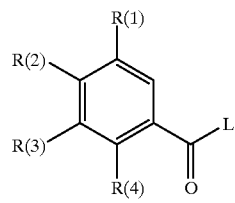

with guanidine, wherein in formula II, R(1) to R(4) have the meaning indicated in claim 1, and L is a nucleophilically substitutable leaving group.

6. A pharmaceutical composition, comprising a compound according to claim 1 together with diluents, excipients or other suitable pharmaceutically acceptable carriers.

7. A method of treating states of shock, comprising administering to a patient in need thereof an effective amount of a compound according to claim 1, or a pharmaceutically tolerable salt thereof.

8. A method of protecting and preserving organs by protection against pathological hypoxic or ischemic situations for surgical operations and organ transplantation, comprising administering to said organs an effective amount of a compound according to claim 1 or a pharmaceutically tolerable salt thereof.

9. A method of preserving and storing of transplants for surgical measures by protection against pathological hypoxic or ischemic situations, comprising administering to said transplant an effective amount of a compound according to claim 1, or a pharmaceutically tolerable salt thereof.

* * * * *